(12) United States Patent
Miyahara

(10) Patent No.: US 7,565,831 B2
(45) Date of Patent: Jul. 28, 2009

(54) PRODUCTION METHOD OF INDENTATION CURVE AND HARDNESS TEST METHOD

(75) Inventor: Kensuke Miyahara, Tsukuba (JP)

(73) Assignee: National Institute for Materials Science, Ibaraki (JP)

( * ) Notice: Subject to any disclaimer, the term of this patent is extended or adjusted under 35 U.S.C. 154(b) by 448 days.

(21) Appl. No.: 11/589,893

(22) Filed: Oct. 31, 2006

(65) Prior Publication Data
US 2007/0113628 A1 May 24, 2007

(30) Foreign Application Priority Data
Oct. 31, 2005 (JP) ............................. 2005-316059

(51) Int. Cl.
*G01N 3/48* (2006.01)
(52) U.S. Cl. ......................................................... 73/81
(58) Field of Classification Search .................... 73/81, 73/82
See application file for complete search history.

(56) References Cited

U.S. PATENT DOCUMENTS

2003/0196480 A1 * 10/2003 Anderberg ..................... 73/81

OTHER PUBLICATIONS

Mark R. VanLandingham, "Review of Instrumented Indentation", Journal of Research of the National Institute of Standards and Technology, vol. 108, No. 4, Jul.-Aug. 2003, pp. 249-265.

* cited by examiner

*Primary Examiner*—Robert R Raevis
(74) *Attorney, Agent, or Firm*—Wendroth, Lind & Ponack, L.L.P.

(57) ABSTRACT

A production method of an indentation curve is given, in which when an indentation curve showing a relationship between indentation force and indentation depth in a process of indenting an indenter into a surface of a sample is produced, a measurement range using an (i−n)th (here, i and n are natural numbers) measurement value as a reference is provided, and the indentation depth or indentation force is temporarily measured when the indentation force or indentation depth is gradually changed, respectively, and when a temporarily measurement value obtained by the temporarily measurement is out of the determination range, indentation depth at the relevant indentation force or indentation force at the relevant indentation depth is measured and set as an ith measurement value, or the temporarily measurement value is used as the ith measurement value.

20 Claims, 16 Drawing Sheets

(a)

(b)

(a)

(b)

(a)

(b)

(1)

(2)

PRODUCTION METHOD OF INDENTATION CURVE AND HARDNESS TEST METHOD

TECHNICAL FIELD

The invention of the application relates to a production method of an indentation curve and a hardness test method. More particularly, the invention relates to a production method of an indentation curve that enables production of an indentation curve more accurately and efficiently, and a hardness test method using the indentation curve.

BACKGROUND ART

A micro hardness test or a super-micro hardness test, which can examine a mechanical property of a microstructure of a material, are expansively used as a measurement method of a material in wide fields such as semiconductor and micro machining in recent years.

In the micro hardness test or the super-micro hardness test (hereinafter, simply called micro hardness test and the like), a method is widely used, in which a relationship between indentation force (F) and indentation depth (h) in an indentation process of indenting an indenter into a surface of a sample, so-called an indentation curve is obtained to measure a property of a material such as hardness. This is because since size of impression produced in a surface of the sample is extremely small in the micro hardness test and the like, 1 μm or less, compared with a macro hardness test such as the Vickers hardness test, size of impression is hardly measured by a light microscope.

Moreover, in the micro hardness test and the like, it is not sufficient only to obtain indentation depth at the maximum load when the indenter is indented into the sample, and it is required to obtain a relationship between continuous indentation force from load to unload and indentation depth, that is, an indentation curve, as schematically shown in FIG. 1.

Furthermore, to evaluate a property of a material from the indentation curve obtained in this way, in some cases, it is enough to simply compare the magnitude of the indentation depth at the maximum indentation force and the like, however, in other some cases, the indentation curve is used for fitting to a particular function form in order to calculate shape compensation of the indenter or a parameter such as hardness (for example, see patent literatures 1 and 2), or used for determining a position of a characteristic point as schematically shown in FIG. 2 (for example, see patent literature 3). In this case, a more accurate indentation curve having no blank and high data point density is required.

As a method of obtaining such an indentation curve, a load test by one of (A) load (indentation force) control method, or (B) displacement (indentation depth) control method is generally performed. The (A) load control method or the (B) displacement control method is for discretely obtaining a relationship between load and displacement by measuring displacement or load while controlling a tester such that a load range (df) applied to a sample or a displacement range (dh) is to be a certain setting value, respectively. FIGS. 3 and 4 schematically show indentation curves obtained by the (A) load control method and the (B) displacement control method respectively, and show actually measured points (data points) by black circles. As known from FIGS. 3 and 4, the (A) load control method has a feature that the data point density is typically high compared with the displacement control method in a large gradient region of the indentation curve, for example, at a high load side and in an unloading process, or in a case of a hard sample, and stable control can be performed compared with the displacement control method. In a typical hardness test, results at the same load are traditionally compared in many cases, and results at various levels of load below specified load can be obtained by the method. The other (B) displacement control method has a feature that the data point density is typically high compared with the load control method in a small gradient region of the indentation curve, for example, at a low load side or in a case of a soft sample.

(For example, refer to patent literature 3, non-patent literature 2, and non-patent literature 3.)
[Patent literature 1] JP-A-11-271202.
[Patent literature 2] JP-A-9-318516.
[Patent literature 3] JP-A-2004-81546.

However, in an actual micro hardness test and the like, since the gradient of the indentation curve is different between hard and soft portions of a sample, an optimum load range (df) or displacement range (dh) is different depending on a measurement place. Specifically, in the case of the load control method, since the gradient of the indentation curve is large in a test at a hard portion, the load range (df) can be set relatively large, however, the load range (df) needs to be conversely decreased in a test at a soft portion. Here, when the sample is uniform, the optimum load range (df) can be determined by performing tests several times. However, when the sample is not uniform, for example, when hardness has distribution, there have been problems that since results are essentially different depending on places, the test must be performed at an unnecessary small load range (df) on the assumption that the softest portion may be tested to secure a certain data point density, consequently much time is required for measurement, and the test is easily influenced by temperature drift. Such problems are the same in the displacement control method in which sufficient data point density is not obtained for various indentation curves having different gradients, or an experiment at an unnecessarily small displacement range (dh) is forced to be conducted.

Moreover, in the case of the indentation curve having the characteristic point as shown in FIG. 2, there has been a problem that the optimum load range (df) or displacement range (dh) is hard to be set in the case that a position of the characteristic point can not be expected.

Thus, the invention of the application was made in the light of the circumstances as above, and has an issue of providing a new production method of the indentation curve, which solves the problems in the related art, and enables securing sufficient data point density in various indentation curves having different gradients without changing setting by an observer, and a new micro hardness test method.

DISCLOSURE OF INVENTION

As a solution of the problems, first, the invention of the application provides a production method of an indentation curve, when an indentation curve showing a relationship between indentation force and indentation depth in a process of indenting an indenter into a surface of a sample is produced, which comprises, setting a determination range based on an (i−n)th (here, i and n are natural numbers) measurement value as a reference, temporarily measuring a indentation depth or indentation force when the indentation force or indentation depth is gradually changed respectively, and measuring the indentation depth at the relevant indentation force or indentation force at the relevant indentation depth when a temporary measurement value obtained by the temporarily measurement is out of the determination range to set it as an ith measurement value.

In the production method of the indentation curve above mentioned, second, the invention of the application provides a production method which comprises setting the determination range based on an (i−1)th (here, i is an natural numbers) measurement value as a reference; third, it provides a production method which comprises using a temporarily measurement value as an ith measurement value when the temporarily measurement value obtained by the temporarily measurement is out of the determination range; fourth, it provides a production method wherein measurement speed is increased by decreasing the number of measurement times at one temporarily measurement point; fifth, it provides a production method wherein conversion speed is increased in the temporarily measurement by reducing accuracy of A/D conversion of the temporarily measurement value from an analog signal to a digital signal; sixth, it provides a production method wherein indentation depth when indentation force is gradually changed is temporarily measured in a rage where a change level in indentation force is large, and indentation force when indentation depth is gradually changed is temporarily measured in a range where a change level of the indentation depth is large; seventh, it provides a production method wherein the determination range is in a circular, elliptic, or rectangular shape using an (i−1)th measurement point as a center.

Moreover, eighth, the invention of the application provides a hardness test method which comprises obtaining hardness of a micro area of a sample into which the indenter is indented from one of the above indentation curves.

The above invention of the application, in obtaining the indentation curve in the micro hardness test or the super-micro hardness test, previously defines a range (determination range) to be not used for a subsequent measurement value, that is, a range to be necessarily used, and dynamically monitors both of the indentation force (load) and the indentation depth (displacement) rather than one of them, and uses the indentation force or indentation depth as a measurement point at the timing when it enters the range to be used.

BEST MODE FOR CARRYING OUT THE INVENTION

The invention of the application has features as above, and hereinafter an embodiment of the invention is described.

In a production method of an indentation curve of the invention of the application, when an indentation curve showing a relationship between indentation force and indentation depth in process of indenting an indenter into a surface of a sample is produced, a measurement range using an (i−n)th measurement value as a reference is provided, and the indentation depth or indentation force is temporarily measured when the indentation force or indentation depth is gradually changed, respectively, and when a temporarily measurement value obtained by the temporarily measurement is out of the determination range, indentation depth at the relevant indentation force or indentation force at the relevant indentation depth is measured and set as an ith measurement value.

The temporarily measurement in the invention of the application can widely include methods in which even if accuracy is reduced compared with actual measurement (real measurement), measurement can be performed correspondingly at higher speed. To realize increase in speed of measurement, specifically, it can be exemplified that, for example, accuracy in A/D conversion is reduced, or average number of measurement values is decreased.

The invention of the application can be used for production of an indentation curve with a sample in any optional material and structure as an object, and in particular, effectively used for production of an indentation curve of a micro hardness region or a super-micro hardness region. Moreover, in the invention of the application, when the indentation curve is produced, an indenter in any optional shape can be used for the indenter, and various types such as a cantilever type or an inboard lever type can be used for indentation of the indenter.

Figure 5:
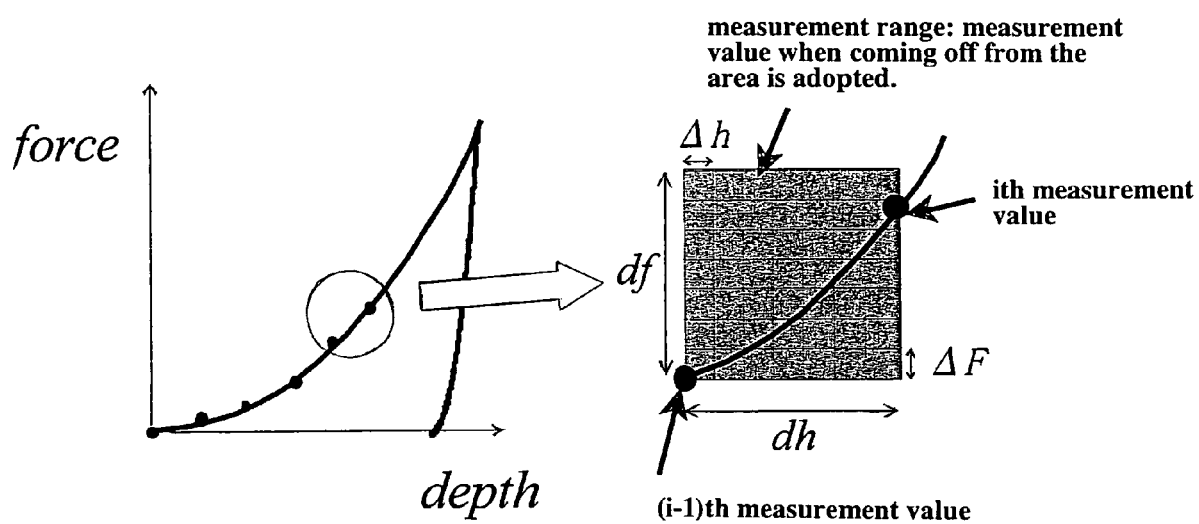
FIG. 5 shows a view schematically explaining an aspect of acquiring an ith measurement point in the method of the invention of the application.

It is peculiar for the present invention to set a determination range based on an (i−n)th measurement value as a reference in obtaining the ith measurement value, as shown in FIG. 5 diagrammatically. Concretely, an indentation depth or indentation force when the indentation force or indentation depth is changed little by little ($\Delta F$ or $\Delta h$), is temporarily measured respectively. The main measurement is done when temporarily measurement value is out of the determination range, and an ith measurement is performed. Here, i indicates the number of measurement times, and i=1, 2, 3 . . . is given. n indicates a value used for indicating a measurement value as a reference of the determination range, and can be any optional natural number. Hereinafter, regarding setting of the determination range, the invention of the application is described using a case of n=1, that is, a case of setting the determination range using an (i−1)th measurement value as the reference as a typical example for convenience, however, the invention of the application is not obviously limited to this. A 0th measurement point can be regarded to be in a case that both of the indentation depth and the indentation force are 0.

As the determination range, any optional range can be set, for example, using the (n−1)th measurement value as the reference, however, since a temporarily measurement value within the determination range are not used as a measurement value, it can be determined considering such that an ith measurement value is obtained from the (n−1)th measurement value at an appropriate interval. That is, for example, an interval between desired measurement points in the indentation curve can be set as the determination range. The determination range may not necessarily be fixed through measurement, and when behavior of the indentation curve can be roughly recognized, the determination range can be changed during measurement, for example, a load direction in the determination range is set narrow in a small load range, and the load direction in the determination range is set wide in a large load range. In setting of the determination range, in the case of $n \geq 2$, slightly wide determination range can be set compared with a case of n=1 in consideration that a measurement value as a reference becomes more distant.

In the method of the invention of the application, when the indentation curve is produced, indentation force or indentation depth is gradually changed, and indentation depth or indentation force at that time is temporarily measured respectively. While a temporarily measurement value obtained by the temporarily measurement is approximately in the determination range initially, when it is out of the determination range, indentation depth or indentation force at the relevant indentation force or indentation depth is measured as the ith measurement value. Here, the temporarily measurement value when it is out of the determination range can be used as the ith measurement value. Here, the gradually changed indentation force ($\Delta F$) or indentation depth ($\Delta H$) can be optionally set. More specifically, it is exemplified that, for example, (1) indentation force or indentation depth in a range of about ½₀ to ½₁₀₀ of the determination range is set as a temporary standard. This is a method that the determination range is divided into about 10 to 20 sections, so that the temporarily measurement is gradually advanced, as an image. Moreover, (2) accuracy of apparatus can be set as $\Delta F$ or $\Delta h$. Actually, however finely the $\Delta F$ or $\Delta h$ is set compared with accuracy of a hardness tester or the like, it will be meaningless, therefore it can be set as finely as possible to the extent allowed by capability of the apparatus. As an image, this is a way that the temporarily measurement is securely advanced while being chopped safely and finely, however, time is correspondingly required. On the other hand, (3) a load range or a displacement range set in a usual (conventional) method can be set as the $\Delta F$ or $\Delta h$. While an unnecessarily fine value is forced to be set as the load range or displacement range in the usual method, the unnecessarily fine value can be utilized for measurement as the $\Delta F$ or $\Delta h$ in the invention of the application.

FIG. 5 schematically illustrates this, showing an aspect that the (i−1)th measurement point has been obtained, and the subsequent ith measurement point is obtained. For example, in the case of this figure, a range connecting four points of (0, 0), (df, 0), (df, dh) and (0, dh) to one another is defined as the determination range with the (i−1)th measurement point as a reference (origin) of coordinates. Here, the df and dh can be considered to correspond to the load range and the displacement range set in the usual measurement of the indentation curve. $\Delta F$ and $\Delta h$ are respectively the load range and the displacement range changed when temporarily measurement. In the method of the invention of the application, either the load or displacement might be changed. For instance, when the load is changed, indentation force is not increased to the load range (df) of the indentation force at once unlike the usual method, indentation depth (h) is temporarily measured sequentially while indentation force is gradually changed by a slight level ($\Delta F$), and when an obtained measurement value ($x \cdot \Delta F$ or h) is out of the determination range, the ith measurement is performed for the first time, or the measurement value is used as the ith measurement value. For example, in the case of FIG. 5, in the case that the value gets out of the determination range at a side of an upper side of the range shown by a square in the figure, the method is equivalent to the load control method, and in the case that the value gets out of the range at a side of a right side, the method is equivalent to the displacement control method. Therefore, it can be regarded that a more accurate method is dynamically selected between the load control method and the displacement control method in each measurement point.

According to such dynamical selection of the measurement method, the indentation curve can be obtained highly accurately without need of changing setting of apparatus by a user every time.

Figure 6:
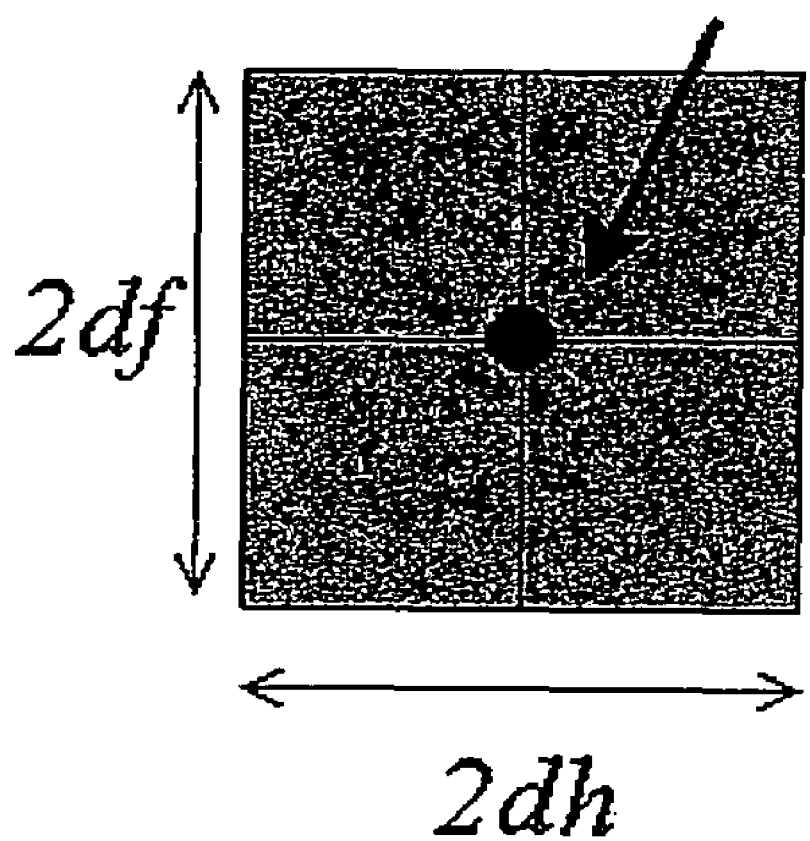
FIG. 6 shows a view schematically illustrating a setting area of a determination range in the method of the invention of the application.

While description was made assuming only a case that the indentation curve extends in an upper right direction for convenience in FIG. 5, since a case that the curve extends in a lower left direction may be considered, for example, as an unload curve, a region having ranges in vertical and horizontal directions is desirably used for setting a more general determination range, for example, as shown in FIG. 6. While a configuration of the determination range is not limited, more generally, it is shown as a preferable example that the determination range is set in a rectangular shape such as a square or various rectangles, a rhombic shape, or a circular or elliptic shape for making distances between measurement values to be constant. Moreover, it can be considered that the measurement range is varied depending on indentation force or indentation depth as described before.

Furthermore, while a case of gradually increasing the indentation force by the slight level ($\Delta F$) is shown for convenience in FIG. 5, it can be obviously considered that the indentation depth is gradually increased by a slight level ($\Delta h$) in the same way. To further improve accuracy of the indentation curve, for each ith measurement, the indentation depth may be temporarily measured while the indentation force is gradually changed in a range where a change level of the indentation force is expected to be large, or the indentation force may be temporarily measured while the indentation depth is gradually changed in a range where a change level of the indentation depth is expected to be large.

As described above, the temporarily measurement in the invention of the application can widely include methods in which even if accuracy is reduced compared with actual measurement (real measurement), measurement can be performed correspondingly at higher speed. To realize increase in speed of measurement, specifically, it can be exemplified that, for example, accuracy in A/D conversion is reduced, or average number of measurement values is decreased.

A way of reducing accuracy in A/D conversion is to sacrifice accuracy when an analog signal (here, voltage) is converted into a digital signal (a value to be stored in a memory of a computer or the like) to increase speed in a hardness tester or the like used generally. For example, when a signal in a range of 0 to 10 V is converted, accuracy (pitch) is as shown in the following Table 1 depending on the bit number of conversion.

TABLE 1

| | |
|---|---|
| in the case of 8 bit | $10 \text{ V}/2^8 = 39$ mV |
| | (0.4% of full scale, 10 V) |
| in the case of 12 bit | $10 \text{ V}/2^{12} = 2.4$ mV |
| | (0.02% of full scale, 10 V) |
| in the case of 16 bit | $10 \text{ V}/2^{16} = 0.15$ mV |
| | (0.0015% of full scale, 10 V) |

While accuracy is improved by increasing the bit number, time for the A/D conversion is increased at that time. Therefore, the bit number is decreased to an appropriate level to improve conversion speed. Alternatively, it is possible to be selectable that accuracy is reduced so that measurement is performed correspondingly at higher speed to it depending on a type of an A/D conversion board to be used. For example, the A/D conversion unit KL-4AD manufactured by Keyence Corporation is used, thereby the following high speed mode can be used for the temporarily measurement.

[normal] accuracy: 0.2% of full scale, conversion speed 1.6 ms

[high speed] accuracy: 0.5% of full scale, conversion speed 0.2 ms

The other way, the way of decreasing average number of measurement values is a way in which since a typical measurement value in various kinds of mechanical measurement includes accidental errors due to various reasons, measurement is performed several times at one measurement point rather than one time, and an average value of the measurement is usually used. Similarly, in obtaining a typical indentation curve, measurement is performed, for example, about 100 to 1000 times at one measurement point rather than one time, then the values are subjected to A/D conversion and an average value of them is used. While increase in the averaging number brings improvement in accuracy, time for measurement is increased, therefore a method can be used in the temporarily measurement, in which the averaging number at one measuring point (that is, the number of measurement times for temporarily measurement) is decreased, so that accuracy is sacrificed to decrease measurement time. In consideration of such points, for example, compared with the usual measurement, speed in the A/D conversion is increased to 10 times, and the averaging number is decreased to $\frac{1}{10}$, thereby the temporarily measurement can be performed at a speed as high as 100 times. It is essence of the invention of the application to skillfully use the method of the high speed "temporarily measurement" to the utmost.

In addition to the above exemplification, it can be considered that since the temporarily measurement does not store data, for example, time for transfer from a digital signal processor to a personal computer, or time for transfer from the personal computer to a storage device is omitted. Furthermore, it can be considered that when a temporarily measurement value gets out of the determination range, the temporarily measurement value is used for improving accuracy of the ith measurement.

Meanwhile, there is a possibility that the misjudgment occurs when a temporarily measurement value compares with the value of a main measurement since this measurement with the range of the judgment for low accuracy. As a misjudgment in this case, two cases of (I) the case deeming a temporarily measurement within the determination range to be the outside of the determination range and (II) the case deeming a temporarily measurement outside of the determination range to be in the determination range, are thought. However, the influence of a temporarily measurement that cause such a misjudgment can be suppressed to the minimum by doing the main measurement after the temporarily measurement. And, the influence of the misjudgment is small in both cases since, in the case of (I), one originally unnecessary data point is only added and, in the case of (II), the density of the data point only decreases locally and slightly only by $\Delta F$ or $\Delta h$ that is the width of the measurement because the following temporarily measurement is measured at once. Considering the whole of the measurement process, the meaning of the present invention is not lost even if such a misjudgment is caused in only a small part.

When the ith measurement is performed in this way, a similar procedure is sequentially repeated for measurement: (i+1)th . . . , and at the time point when measurement reaches the maximum indentation force or the maximum indentation depth, which is finally required, the measurement can be shifted to an unload process. The unload process can be performed according to the same procedure as above. However, regarding behavior of the indentation curve in the unload process, sufficient data may be generally obtained by the usual load control method, therefore, for example, indentation force $\Delta F$ is made equal to df, and measurement may be switched to be in substantially the same measurement as that in the usual load control method.

Figure 16:
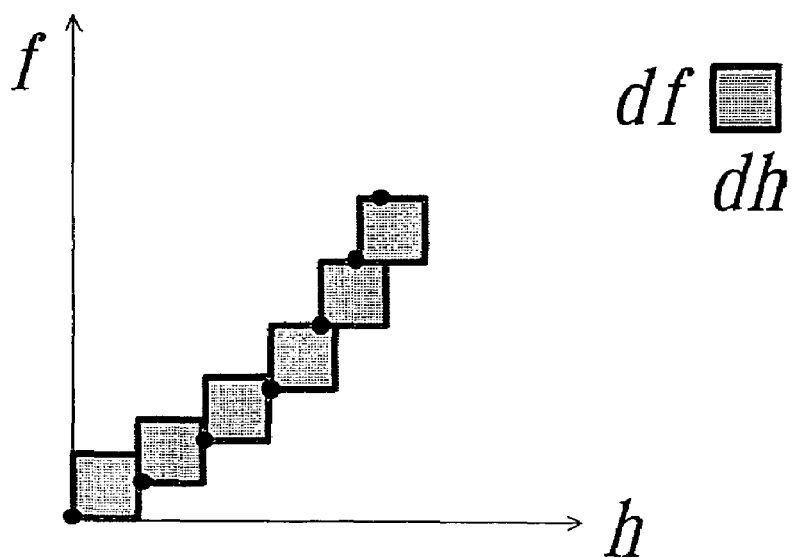
FIGS. 16(*a*) and 16(*b*) show views schematically illustrating a relationship between the indentation curve obtained by the method of the invention of the application and a determination range.
Figure 16:
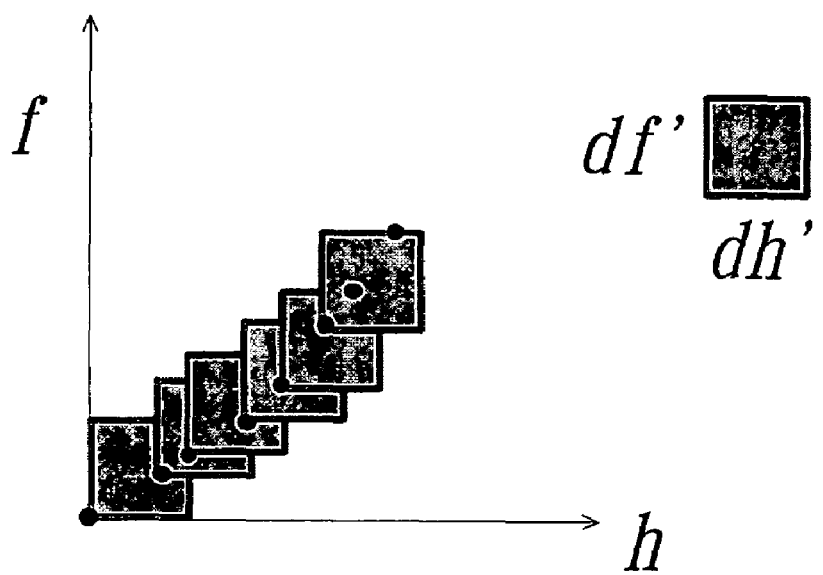

In the case of $n \geq 2$, measurement may be performed according to the usual method before the nth measurement, or may be performed, for example, in setting of n=1 before the mth measurement, and in setting of n=m from the mth measurement. FIG. 16 schematically shows (1) a measurement sample in the case of n=1, and (2) a measurement sample in the case of n=2. From comparison between them, while an indentation curve obtained in the case of n=2 is essentially the same as that obtained in the case of n=1, a value of n can be set in consideration of a measurement object. Moreover, it is obvious that the determination range may be set with an intermediate value (average) between mth and (m+1)th measurement values as a reference in consideration of setting n as both of n=m and n=(m+1).

The above production method of the indentation curve of the invention of the application can be actually realized in industry by using programming by a computer or digital signal processor.

Figure 7:
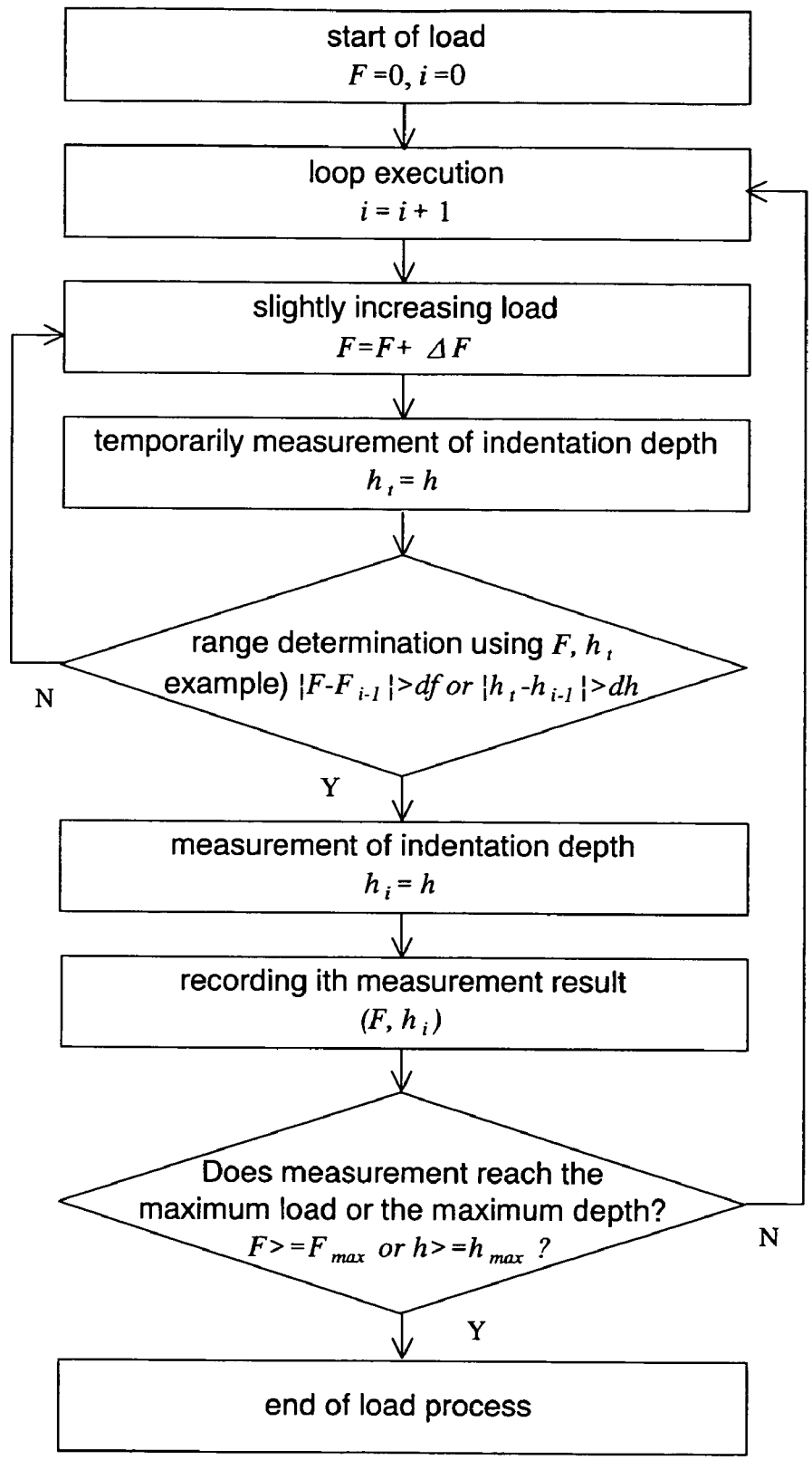
FIG. 7 shows an example of a flowchart in the case of producing a load process of an indentation curve according to the method of the invention of the application.
Figure 8:
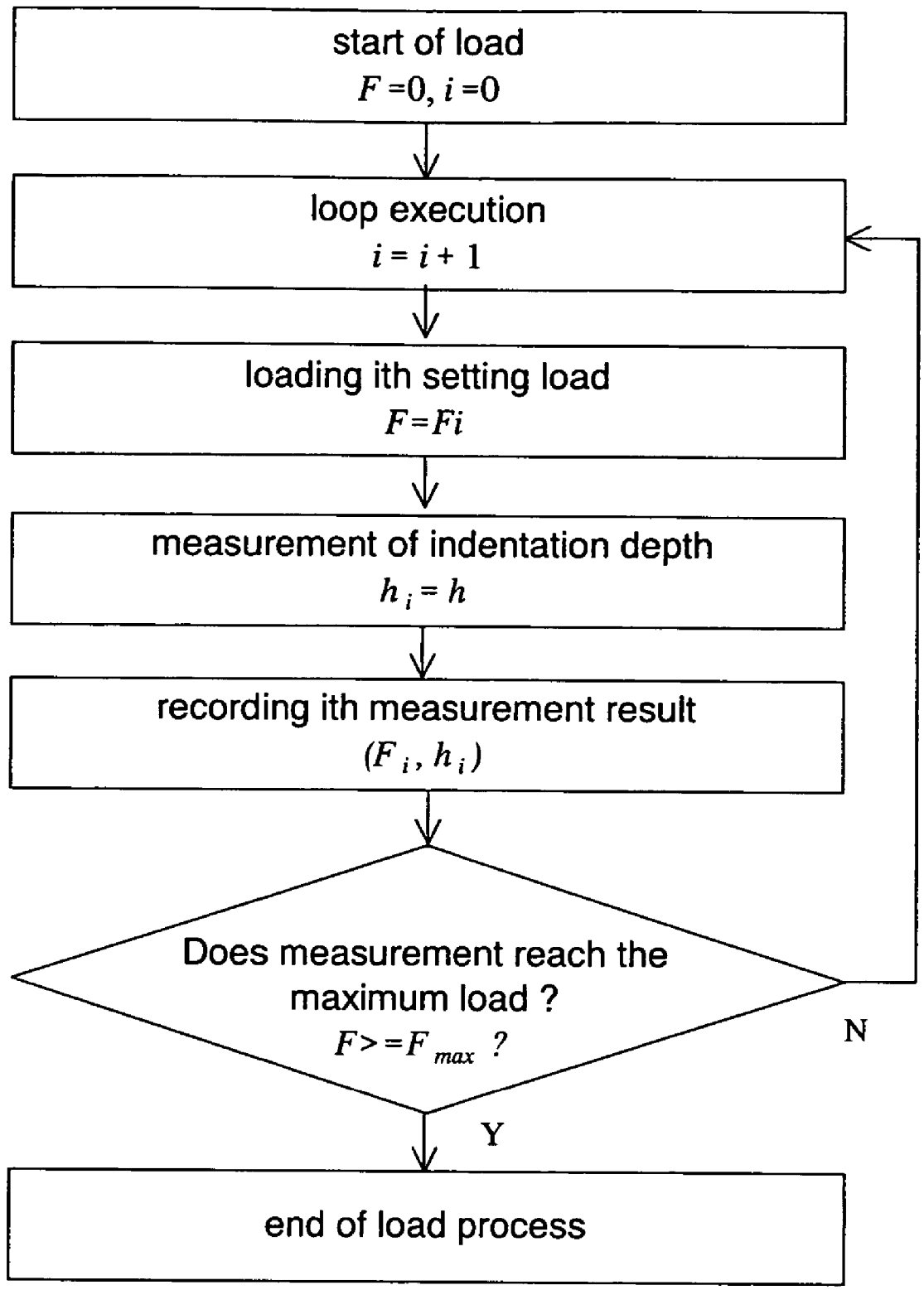
FIG. 8 shows an example of a flowchart in the case of producing a load process of a usual indentation curve.

Thus, an example of a flowchart in the case of producing a load process of the indentation curve according to the method of the invention of the application is illustrated in FIG. 7. In the flowchart of FIG. 7, the determination range illustrated in FIG. 6 is used as a determination range. For comparison, a flowchart of usual load control method is shown in FIG. 8. Reference signs in the figures are as follows.

F: indentation force
h: indentation depth
i: loop variable
Fi: ith measurement point (indentation force, measurement value)
hi: ith measurement point (indentation depth, measurement value)
$F_{max}$: maximum indentation force
$h_{max}$: maximum indentation depth
df: step of indentation force
dh: step of indentation depth
$\Delta F$: increase in indentation force in temporarily measurement
$\Delta h$: increase in indentation depth in temporarily measurement In the usual load control method of FIG. 8, indentation force Fi as an ith setting value is simply applied to a sample, and indentation depth hi at that time is obtained. On the contrary, in the method of the invention of the application, for example, as illustrated in FIG. 7, the indentation force is gradually changed by a slight level (ΔF) while the indentation depth is temporarily measured, and consequently the flow has a double loop structure. Such two-stage measurement is performed, thereby unnecessary measurement is omitted compared with a method of increasing the number of data points by simply reducing df in the usual load control method, consequently necessary measurement can be efficiently performed. Therefore, measurement values can be obtained in an efficient manner rather than overpopulated or depopulated manner, and a highly accurate indentation curve can be obtained.

Moreover, a hardness test method provided by the invention of the application is characterized by obtaining hardness of a micro area of a sample, into which an indenter is indented, from the indentation curve obtained in the above way. The indentation curve and analysis of the curve are important in a micro hardness test and the like, and a more accurate hardness test is realized by using an indentation curve obtained efficiently and accurately.

Hereinafter, the embodiment of the invention of the application is described further in detail while showing examples. It will be obvious that the invention is not limited to the following examples, and various aspects may exist on details.

EXAMPLES

Example 1

Figure 9:
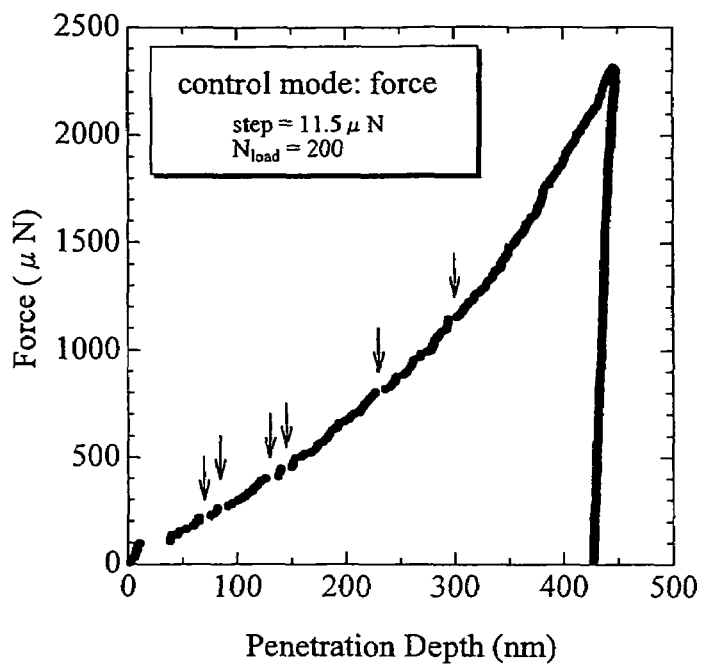
FIGS. 9(*a*) and 9(*b*) show indentation curves obtained by a usual load control method.
Figure 9:
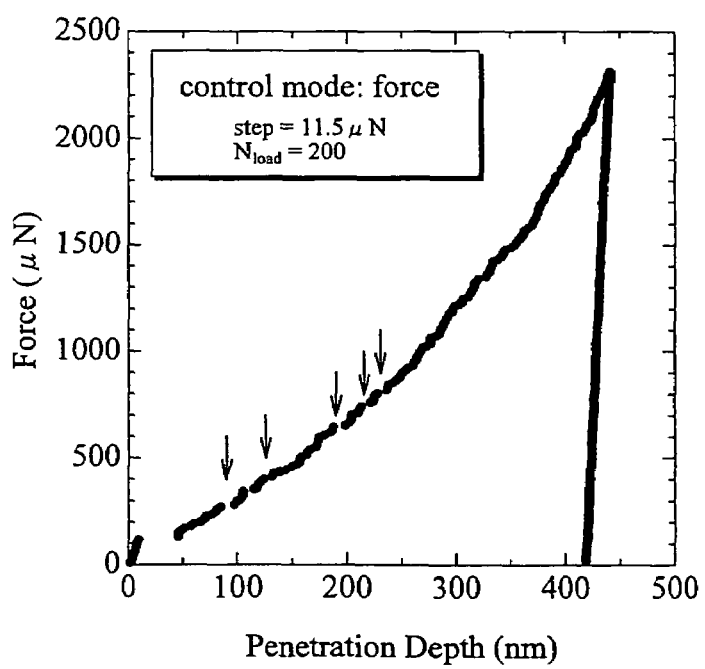
Figure 10:
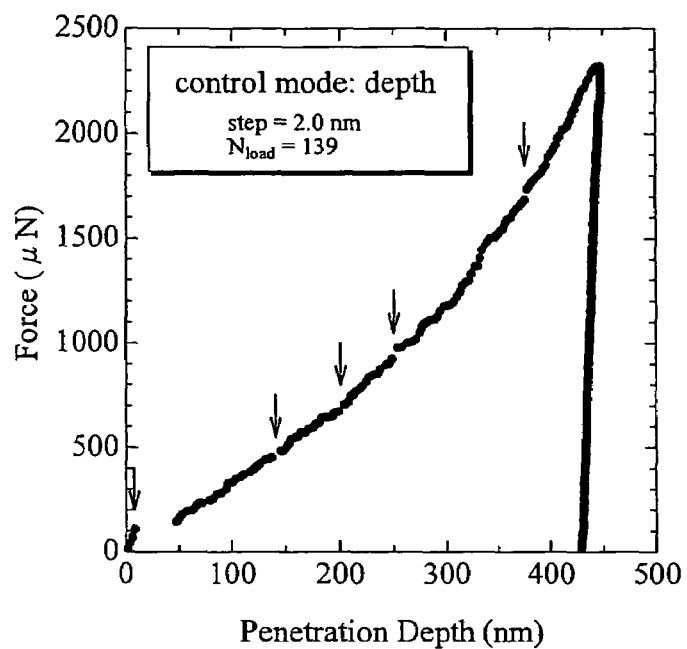
FIGS. 10(*a*) and 10(*b*) show indentation curves obtained by a usual displacement control method.
Figure 10:
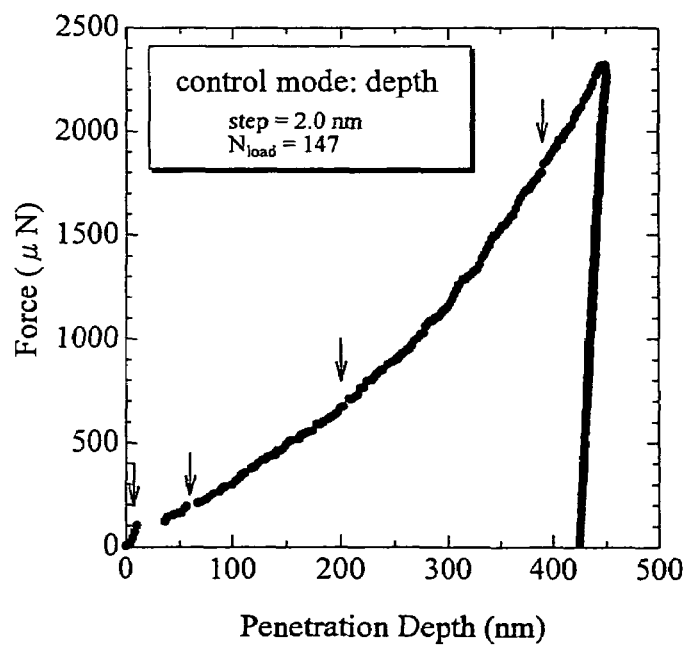
Figure 11:
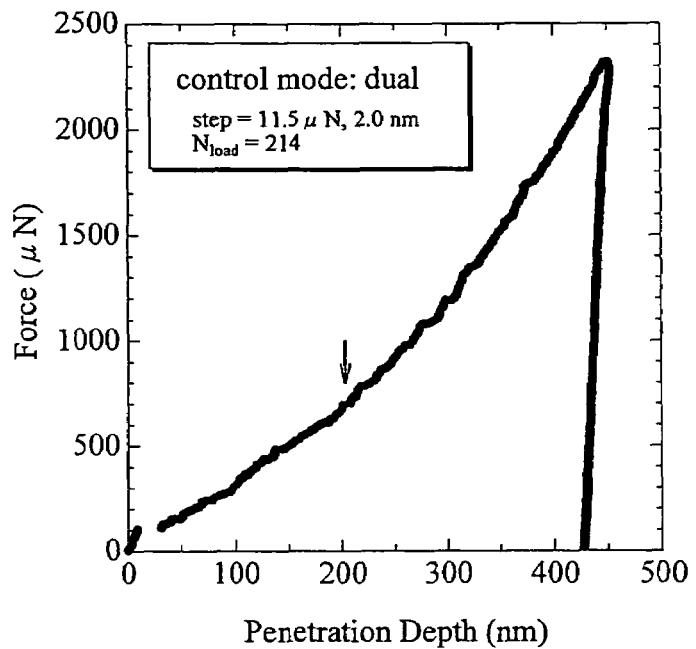
FIGS. 11(*a*) and 11(*b*) show indentation curves obtained by the method of the invention of the application.
Figure 11:
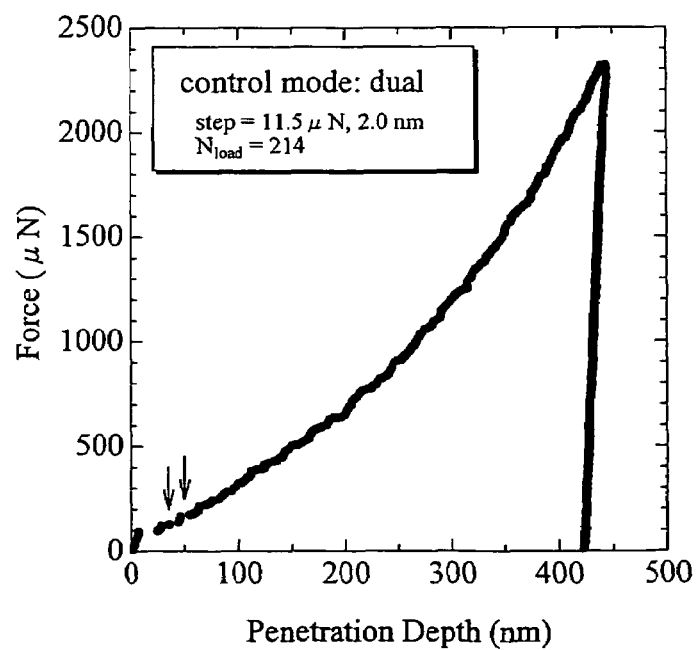
Figure 12:
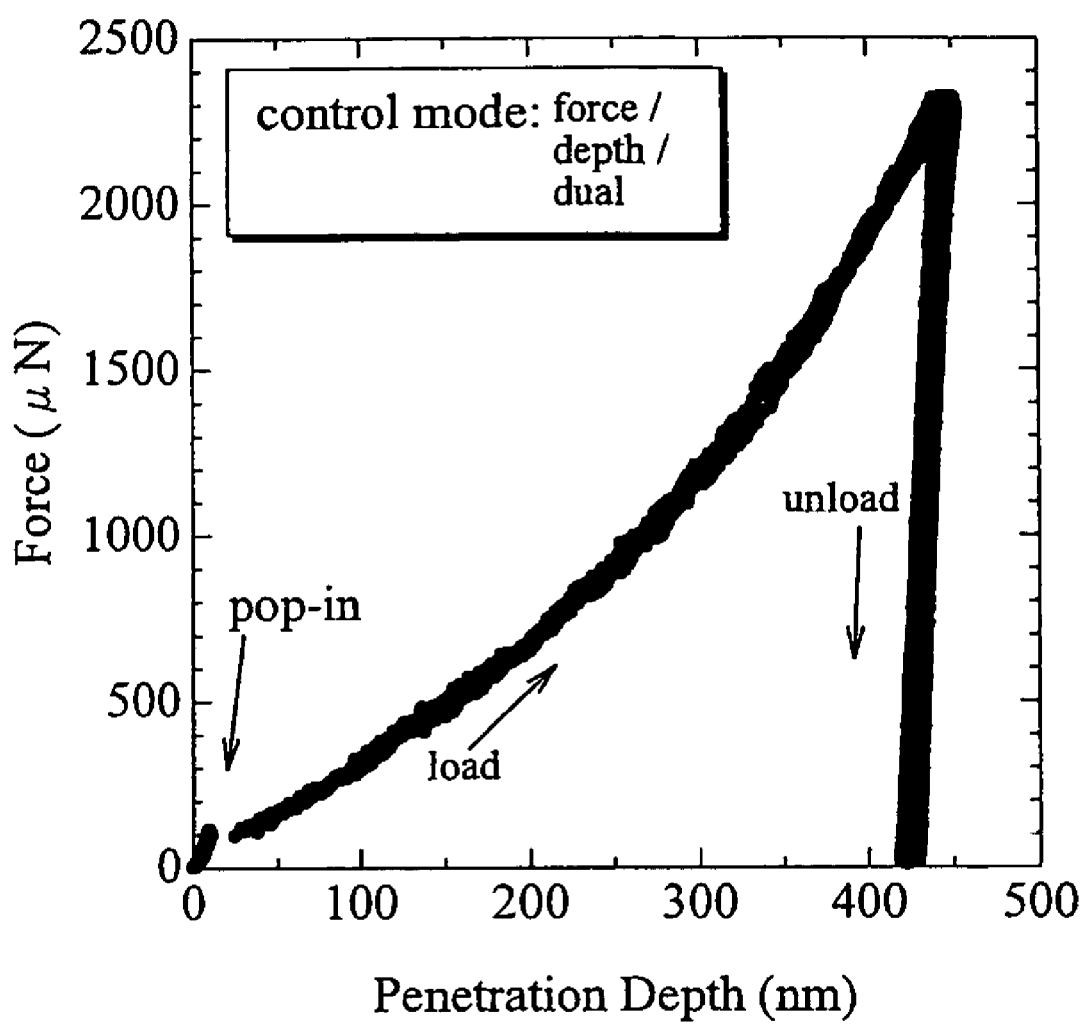
FIG. 12 shows a view of plotting FIGS. 9 to 11 on one graph.

Tungsten single crystal, which was used as a standard sample in a super-micro hardness test, was used for a sample, and indentation curves were produced by various control methods using the same indenter and hardness tester. Results are shown in FIGS. 9 to 12. FIG. 9 shows an indentation curve obtained by a usual load control method, FIG. 10 shows an indentation curve obtained by a usual displacement control method, FIG. 11 shows an indentation curve obtained by the method of the invention of the application, and FIG. 12 shows a view of plotting results of FIGS. 9 to 11 on one graph.

First, it was confirmed from FIG. 12 that plotted points were not significantly displaced in any of indentation curves of FIGS. 9 to 11, therefore absolute values of the indentation curves were not affected by difference in control methods. A discontinuous portion shown by an arrow in the view of FIG. 12 shows a phenomenon called pop-in, which is considered as a transient point from elastic deformation to plastic deformation. Since the pop-in momentarily occurs, it is hard to clearly pick it up.

FIGS. 9(a) and 9(b) show indentation curves obtained by the usual load control method. As a control condition, a load control method with df=11.5 μN as the step df was used, and the number of data points in the load process was 200 in each case. In FIGS. 9(a) and 9(b), regions having thin data points were produced in portions shown by arrows in the views. Since such thin portions are confusing with characteristic points in an indentation curve or the phenomenon such as pop-in, they are not preferable for analysis. Moreover, as previously shown in FIG. 3, it is pointed out that such a phenomenon easily occur in a portion having a small gradient of a curve in the load control method, and results as expected are given again in FIGS. 9(a) and 9(b).

Figure 4:
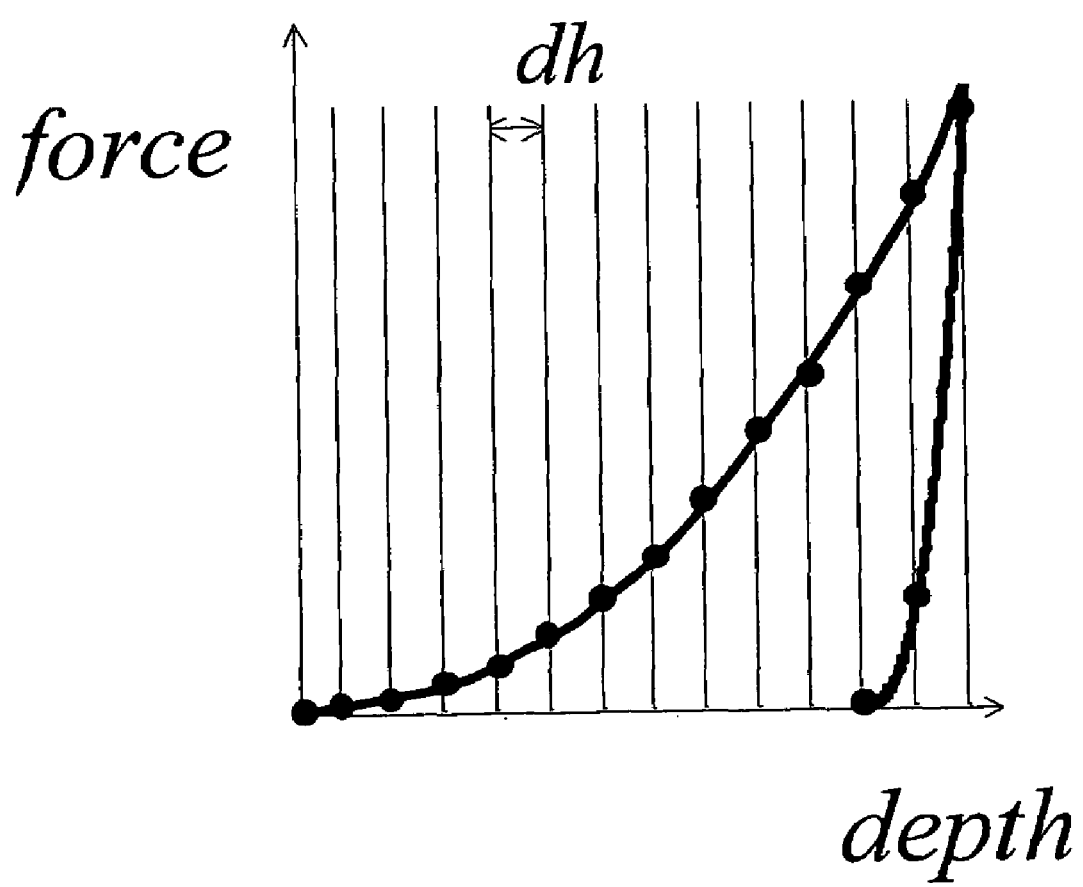
FIG. 4 shows a view schematically illustrating an indentation curve obtained by a displacement control method.

FIGS. 10(a) and 10(b) show indentation curves obtained by the usual displacement control method. However, since the load control method was clearly excellent in the unload process, the displacement control method was used only for the load process. As a control condition, a load control method with dh=2.0 nm as the step dh was used, and the numbers of data points in the load process was 139 and 147. Again in FIGS. 10(a) and 10(b), the regions having thin data points were produced in portions shown by arrows in the views. As previously shown in FIG. 4, it is pointed out that the small number of data points is conspicuous in a portion having a large gradient of a curve in the displacement control method, and results as expected are given again in FIGS. 10(a) and 10(b). In particular, lack of data points is conspicuous in an initial region near the origin. This is not preferable because it causes a problem of increase in error when Young's modulus is obtained by fitting of an elastic area.

FIGS. 11(a) and 11(b) show indentation curves obtained by the method of the invention of the application. As a control condition, a mixed control method with df=11.5 μN as the step df and dh=2.0 nm as the step dh was used, and the number of data points in the load process was 214 in each case. In FIGS. 11(a) and 11(b), it was confirmed that portions having thin data points in the load process were extremely reduced, and an approximately continuous curve was obtained except for pop-in. This is considered to be because, for example, the mixed control method has the number of obtained data points 14 more than that in the load control method, and a data loss region in the load control method is effectively covered by the 14 points and thus data are obtained.

From the results of the example, it was clarified that the method of the invention of the application in effective combination of the load control method and the displacement control method was excellent compared with either of the load control method and the displacement control method.

Example 2

The production method of the indentation curve of the invention of the application and the production method of the indentation curve by the load control method of the usual method were compared by simulation. Preconditions for the simulation were as follows.

An indentation curve is expressed in a form of $F=c \times H^2$ (here, c is a proportional constant depending on material).

A sample is uneven, and has hard and soft portions by 50% each.

One second is required for obtaining one data point (measurement value), including time for A/D conversion and averaging.

Temporarily measurement enables measurement at a speed (that is, 0.01 sec) 100 times higher than a speed in usual measurement.

Figure 13:
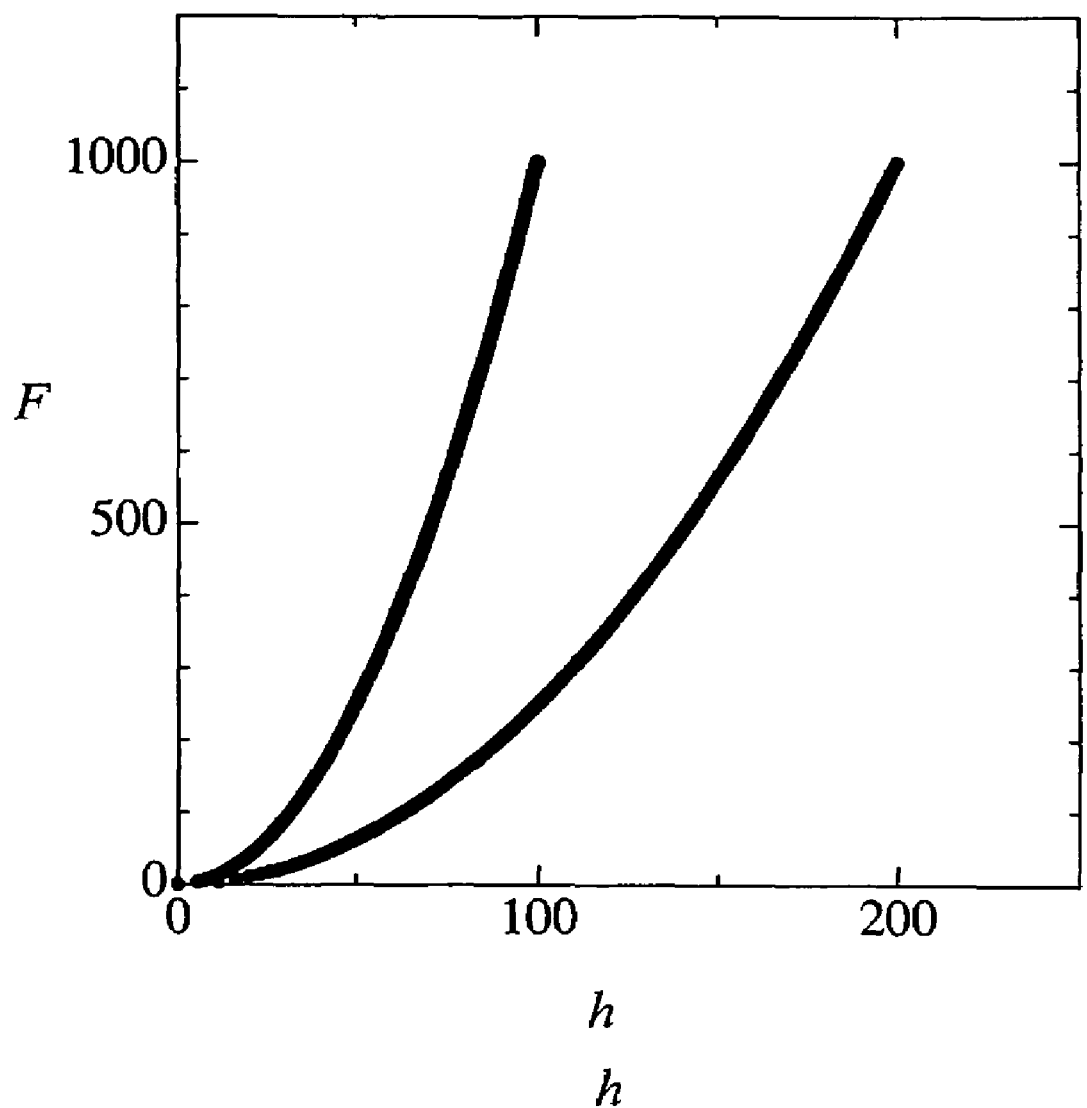
FIG. 13 shows a result of simulation of an indentation curve obtained by the usual method in an example.
Figure 14:
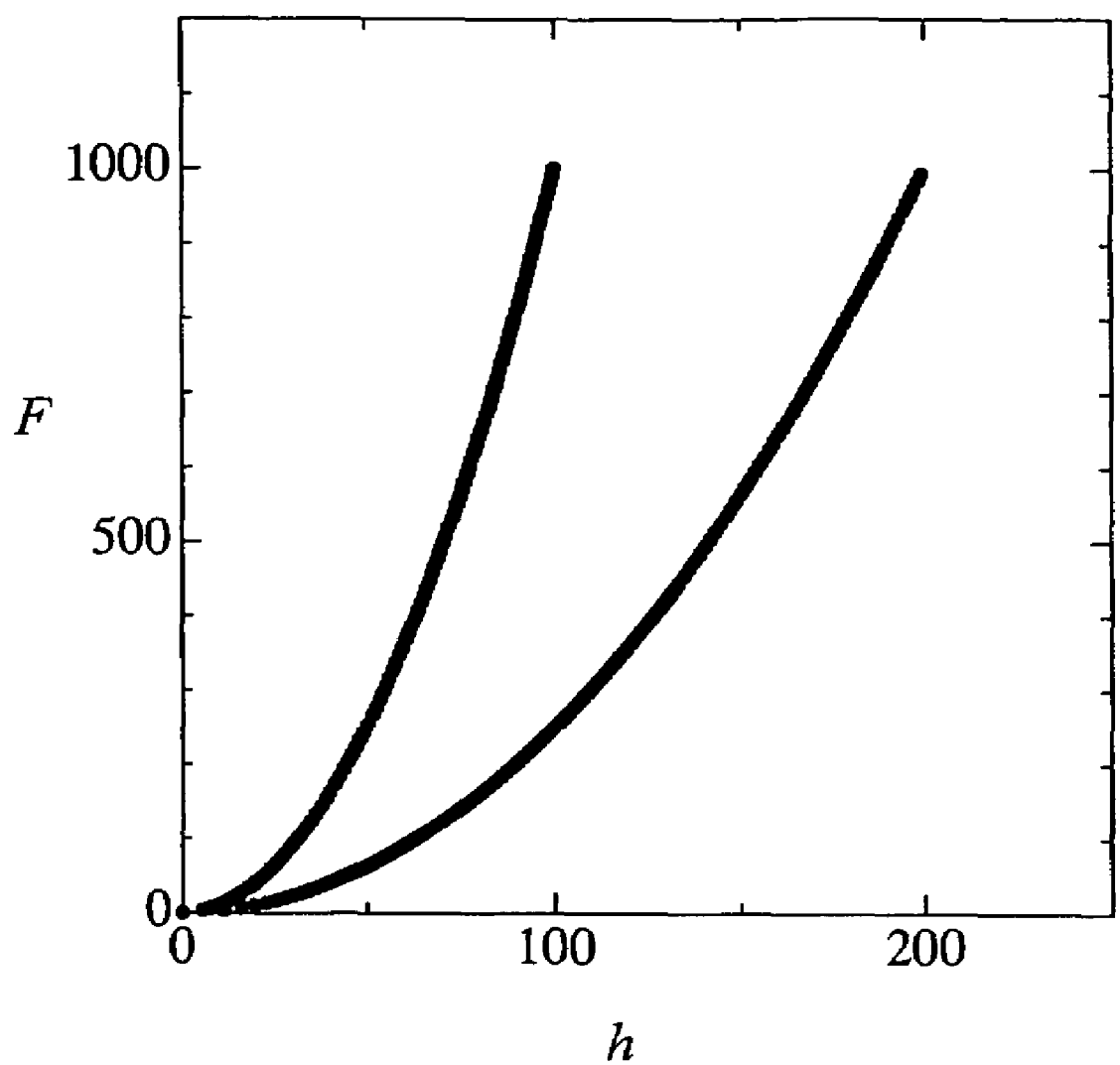
FIG. 14 shows a result of simulation of an indentation curve obtained by the method of the invention of the application in the example.

FIGS. 13 and 14 illustrate results of simulation of indentation curves obtained at the above conditions by the usual method and the method of the invention of the application, respectively. Each of figures shows that a curve at the left in the figure is an indentation curve obtained in a hard portion, and a curve at the right in the figure is an indentation curve obtained in a soft portion. Axes in the figures are in an arbitrary scale, and a curve shows only the load process.

In FIG. 13, df=3.3 is set such that the number of data points of N=301 is given in the usual load control method. Since measurement time of 1 sec is required for obtaining one data point, 301 sec is required for obtaining one indentation curve.

Figure 1:
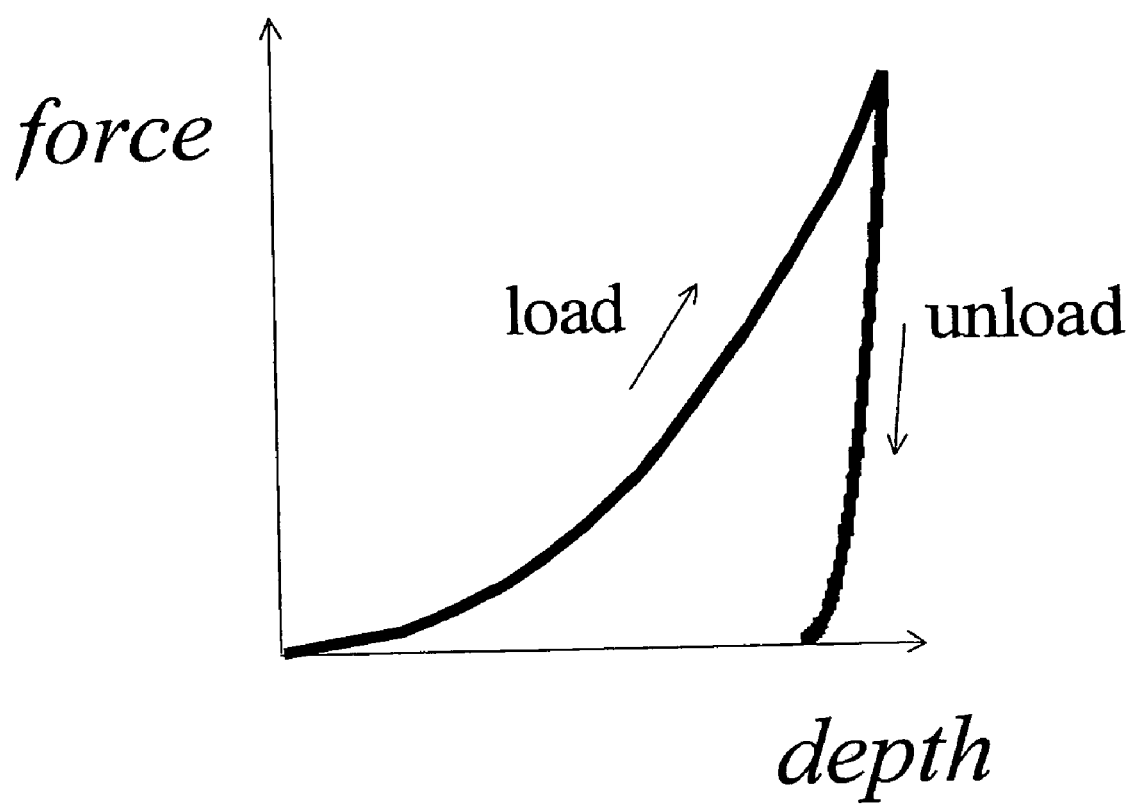
FIG. 1 shows a view a continuous indentation curve from load to unload.
Figure 2:
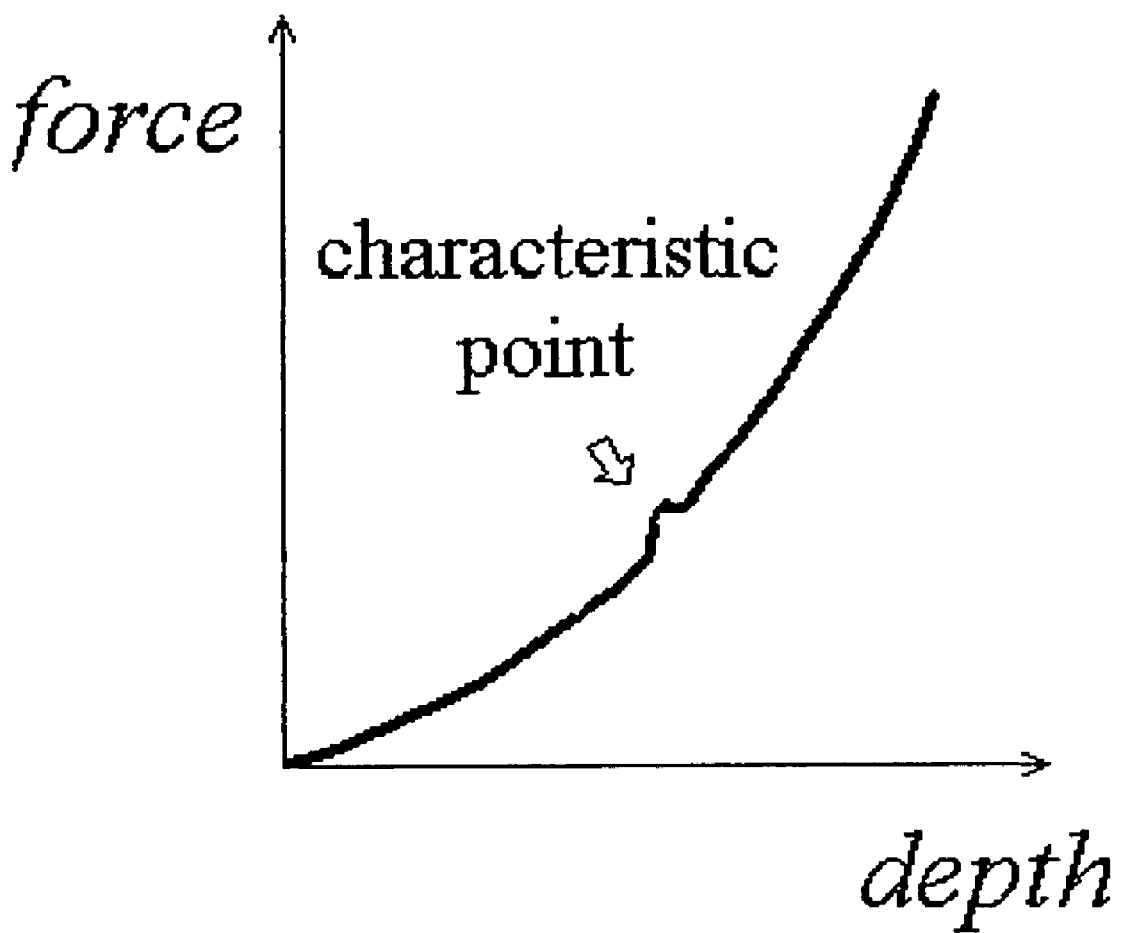
FIG. 2 shows a view illustrating an indentation curve having a characteristic point.
Figure 3:
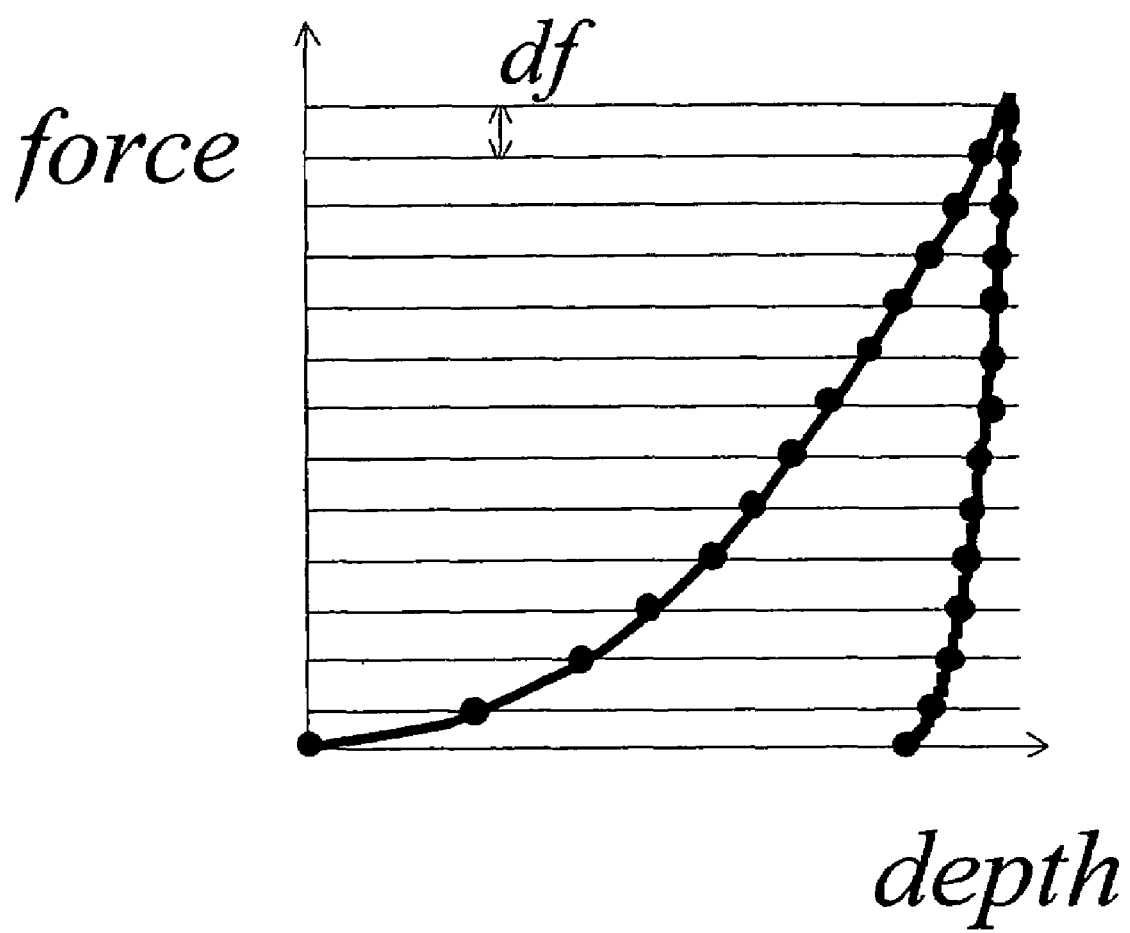
FIG. 3 shows a view schematically illustrating an indentation curve obtained by a load control method.

In FIG. 14, df=10 nm and dh=1 nm are set in the method of the invention of the application, and ΔF=3.3 is set in accordance with the df value in the usual method. While the number of data points is only N=110 in a curve of the hard portion, and only N=139 in a curve of the soft portion in the FIG. 14, it is confirmed that a smooth curve approximately equivalent to that in FIG. 3 is obtained. Time required for measurement is sum of time for real measurement and time for temporarily measurement, which is as shown in Table 2.

TABLE 2

| | | | |
|---|---|---|---|
| hard portion | real measurement times 110 | → | 110 sec |
| | temporarily measurement times 301 | → | 3.01 sec |
| | Total | | 113 sec |
| soft portion | real measurement times 139 | → | 139 sec |
| | temporarily measurement times 301 | → | 3.01 sec |
| | Total | | 142 sec |
| average | | | 127.5 sec |

It is known that according to the method of the invention of the application, measurement at the same accuracy can be performed in half the time or less compared with the usual method. The ratio of measurement time has a higher value as df or dh is set smaller in the usual method.

Figure 15:
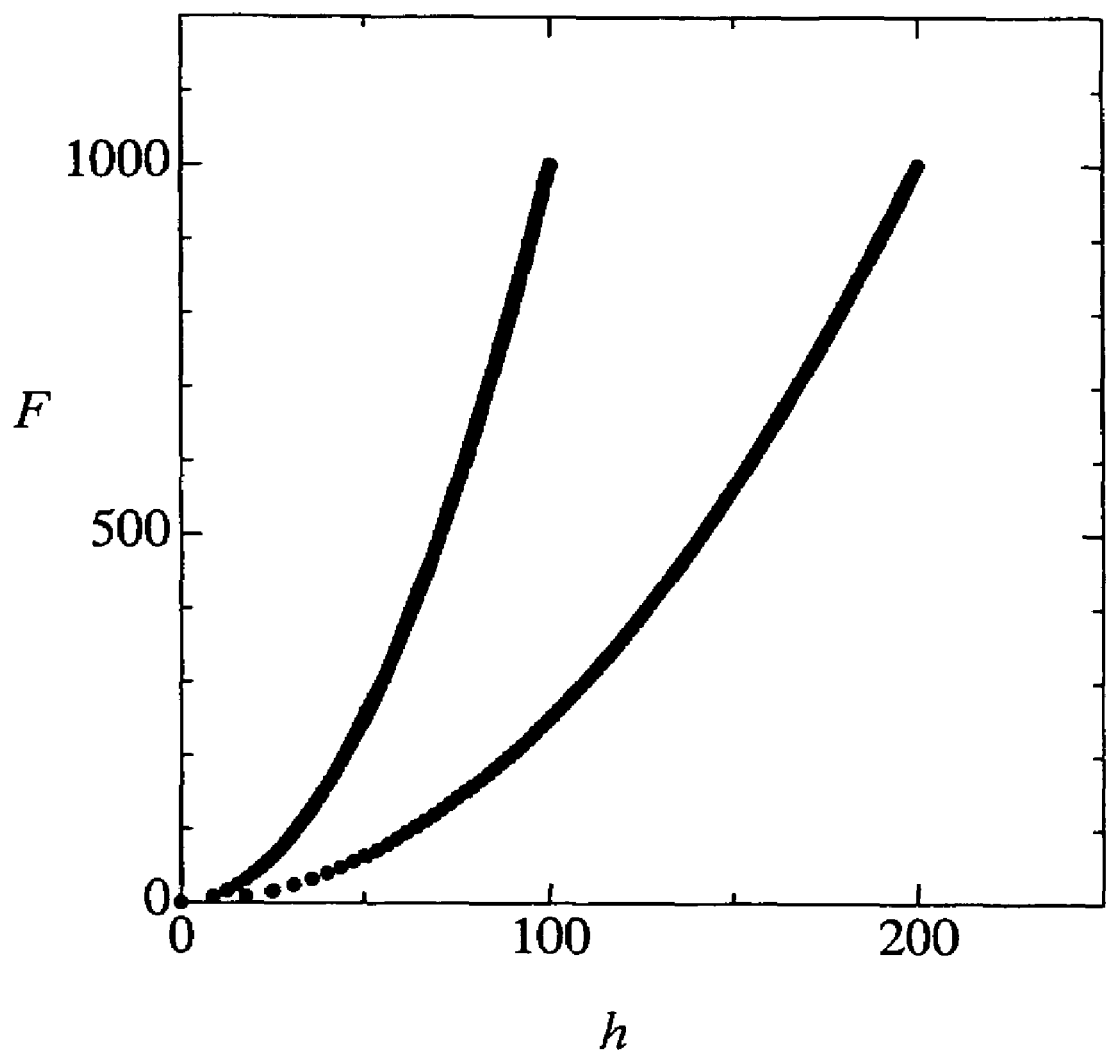
FIG. 15 shows a result of simulation of an indentation curve obtained by the usual method in an example.

For reference, FIG. 15 shows a result of simulation of an indentation curve obtained at a condition of the number of data points of N=127, that is, df=8 nm such that the same measurement time (127 sec) as that in the method of the invention of the application is given in the usual method. It is clear that lack of data points occurs at a low load side, in particular, at a low load side of the indentation curve in the soft portion in FIG. 15.

From the above, it was confirmed that according to the method of the invention of the application, an accurate indentation curve was able to be produced efficiently in a shorter time.

INDUSTRIAL FIELDS OF APPLICATION

According to the production method of the indentation curve of the invention of the application, both of the load and the indentation depth are dynamically monitored by the temporarily measurement, thereby sufficient data point density can be secured in various indentation curves having different gradients without changing setting of a tester and the like by a user.

The invention claimed is:

1. A production method of an indentation curve, when an indentation curve showing a relationship between indentation force and indentation depth in a process of indenting an indenter into a surface of a sample is produced, which comprises:
    setting a determination range based on an (i−n)th (here, i and n are natural numbers) measurement value as a reference,
    temporarily measuring a indentation depth or indentation force when the indentation force or indentation depth is gradually changed respectively, and
    measuring the indentation depth at the relevant indentation force or indentation force at the relevant indentation depth when a temporary measurement value obtained by the temporarily measurement is out of the determination range to set it as an ith measurement value.

2. The production method of the indentation curve according to claim 1, which comprises:
    setting the determination range based on an (i−1)th (here, i is an natural numbers) measurement value as a reference.

3. The production method of the indentation curve according to claim 2, which comprises:
    using a temporarily measurement value as an ith measurement value when the temporarily measurement value obtained by the temporarily measurement is out of the determination range.

4. The production method of the indentation curve according to claim 3, wherein measurement speed is increased by decreasing the number of measurement times at one temporarily measurement point.

5. The production method of the indentation curve according to claim 4, wherein conversion speed is increased in the temporarily measurement by reducing accuracy of A/D conversion of the temporarily measurement value from an analog signal to a digital signal.

6. The production method of the indentation curve according to claim 3, wherein conversion speed is increased in the temporarily measurement by reducing accuracy of A/D conversion of the temporarily measurement value from an analog signal to a digital signal.

7. The production method of the indentation curve according to claim 2, wherein measurement speed is increased by decreasing the number of measurement times at one temporarily measurement point.

8. The production method of the indentation curve according to claim 7, wherein conversion speed is increased in the temporarily measurement by reducing accuracy of A/D conversion of the temporarily measurement value from an analog signal to a digital signal.

9. The production method of the indentation curve according to claim 2, wherein conversion speed is increased in the temporarily measurement by reducing accuracy of A/D conversion of the temporarily measurement value from an analog signal to a digital signal.

10. The production method of the indentation curve according to claim 2, wherein indentation depth when indentation force is gradually changed is temporarily measured in a range where a change level in indentation force is large, and indentation force when indentation depth is gradually changed is temporarily measured in a range where a change level of the indentation depth is large.

11. The production method of the indentation curve according to claim 1, which comprises:
    using a temporarily measurement value as an ith measurement value when the temporarily measurement value obtained by the temporarily measurement is out of the determination range.

12. The production method of the indentation curve according to claim 11, wherein measurement speed is increased by decreasing the number of measurement times at one temporarily measurement point.

13. The production method of the indentation curve according to claim 12, wherein conversion speed is increased in the temporarily measurement by reducing accuracy of A/D conversion of the temporarily measurement value from an analog signal to a digital signal.

14. The production method of the indentation curve according to claim 11, wherein conversion speed is increased in the temporarily measurement by reducing accuracy of A/D conversion of the temporarily measurement value from an analog signal to a digital signal.

15. The production method of the indentation curve according to claim 1, wherein measurement speed is increased by decreasing the number of measurement times at one temporarily measurement point.

16. The production method of the indentation curve according to claim 15, wherein conversion speed is increased in the temporarily measurement by reducing accuracy of A/D conversion of the temporarily measurement value from an analog signal to a digital signal.

17. The production method of the indentation curve according to claim 1, wherein conversion speed is increased in the temporarily measurement by reducing accuracy of A/D conversion of the temporarily measurement value from an analog signal to a digital signal.

18. The production method of the indentation curve according to claim 1, wherein indentation depth when indentation force is gradually changed is temporarily measured in a range where a change level in indentation force is large, and indentation force when indentation depth is gradually changed is temporarily measured in a range where a change level of the indentation depth is large.

19. The production method of the indentation curve according to claim 1, wherein the determination range is in a circular, elliptic, or rectangular shape using an (i−1)th measurement point as a center.

20. A hardness test method, which comprises: obtaining hardness of a micro area of a sample into which the indenter is indented from one of the indentation curves of claim.

* * * * *